United States Patent
Glossop et al.

(10) Patent No.: US 8,263,583 B2
(45) Date of Patent: *Sep. 11, 2012

(54) HYDROCHLORIDE SALT OF 5-[3-(3-HYDROXYPHENOXY)AZETIDIN-1-YL]-5-METHYL-2,2-DIPHENYLHEXANAMIDE

(75) Inventors: Paul Alan Glossop, Sandwich (GB); Kim James, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 324 days.

This patent is subject to a terminal disclaimer.

(21) Appl. No.: 12/530,573

(22) PCT Filed: Mar. 6, 2008

(86) PCT No.: PCT/IB2008/000622
§ 371 (c)(1),
(2), (4) Date: Sep. 9, 2009

(87) PCT Pub. No.: WO2008/135819
PCT Pub. Date: Nov. 13, 2008

(65) Prior Publication Data
US 2010/0113409 A1    May 6, 2010

Related U.S. Application Data

(60) Provisional application No. 60/895,163, filed on Mar. 16, 2007.

(51) Int. Cl.
*A61K 31/397* (2006.01)
*C07D 205/04* (2006.01)

(52) U.S. Cl. .............. 514/210.01; 514/317; 514/408; 546/229; 548/577; 548/950; 548/952

(58) Field of Classification Search ........... 514/210.01, 514/317, 408; 546/229; 548/577, 950, 952
See application file for complete search history.

(56) References Cited

U.S. PATENT DOCUMENTS 7,772,223 B2 *    8/2010   Glossop et al. .......... 514/210.01
2010/0160279 A1 *   6/2010   Glossop et al. .......... 514/210.01

FOREIGN PATENT DOCUMENTS

EP    0948964         10/1999
JP    11100366         4/1999
WO    WO 2007034325    3/2007

OTHER PUBLICATIONS

Borchardt et al. "Pharmaceutical profiling . . . " p. 93-125 (2004).*
Dean "Analytical Chem . . . " p. 10.24-10.26 (1995).*
P. Angeli, et al., Bioorganic and Medicinal Chemistry, vol. 5, No. 9, pp. 731-737, 1997.

* cited by examiner

*Primary Examiner* — Celia Chang
(74) *Attorney, Agent, or Firm* — Lisa A. Samuels

(57) ABSTRACT

This invention relates to the hydrochloride salt of 5-[3-{3-hydroxyphenoxy)azetidin-1-yl]-5-methyl-2,2-diphenyl-hexanamide or derived form thereof and its use as a medicament.

8 Claims, 2 Drawing Sheets

HYDROCHLORIDE SALT OF 5-[3-(3-HYDROXYPHENOXY)AZETIDIN-1-YL]-5-METHYL-2,2-DIPHENYLHEXANAMIDE

This application is the national stage filing of PCT/IB2008/000622 filed Mar. 6, 2008, which claims the benefit of Provisional Patent Application No. 60/895,163 filed Mar. 16, 2007.

This invention relates to the hydrochloride salt of 5-[3-(3-hydroxyphenoxy)azetidin-1-yl]-5-methyl-2,2-diphenylhexanamide and to processes for the preparation of, intermediates used in the preparation of, compositions containing and the uses of, said compound.

The invention also relates to the derived forms of the hydrochloride salt of 5-[3-(3-Hydroxyphenoxy)azetidin-1-yl]-5-methyl-2,2-diphenylhexanamide, including hydrates, solvates and polymorphs thereof.

Cholinergic muscarinic receptors are members of the G-protein coupled receptor super-family and are further divided into 5 subtypes, $M_1$ to $M_5$. Muscarinic receptor subtypes are widely and differentially expressed in the body. Genes have been cloned for all 5 sub-types and of these, $M_1$, $M_2$ and $M_3$ receptors have been extensively pharmacologically characterized in animal and human tissue. $M_1$ receptors are expressed in the brain (cortex and hippocampus), glands and in the ganglia of sympathetic and pirasympathetic nerves. $M_2$ receptors are expressed in the heart, hindbrain, smooth muscle and in the synapses of the autonomic nervous system. $M_3$ receptors are expressed in the brain, glands and smooth muscle. In the airways, stimulation of $M_3$ receptors evokes contraction of airway smooth muscle leading to bronchoconstriction, while in the salivary gland $M_3$ receptor stimulation increases fluid and mucus secretion leading to increased salivation. $M_2$ receptors expressed on smooth muscle are understood to be pro-contractile while pre-synaptic $M_2$ receptors modulate acetylcholine release from parasympathetic nerves. Stimulation of $M_2$ receptors expressed in the heart produces bradycardia.

Short and long-acting muscarinic antagonists are used in the management of asthma and COPD; these include the short acting agents Atrovent® (ipratropium bromide) and Oxivent® (oxitropium bromide) and the long acting agent Spiriva® (tiotropium bromide). These compounds produce bronchodilation following inhaled administration. In addition to improvements in spirometric, values, anti-muscarinic use in chronic obstructive pulmonary disease (COPD) is associated with improvements in health status and quality of life scores.

As a consequence of the wide distribution of muscarinic receptors in the body, significant systemic exposure to muscarinic antagonists is associated with effects such as dry mouth, constipation, mydriasis, urinary retention (all predominantly mediated via blockade of $M_3$ receptors) and tachycardia (mediated by blockade of $M_2$ receptors). A commonly reported side-effect following inhaled administration of therapeutic dose of the current, clinically used non-selective muscarinic antagonists is dry-mouth and while this is reported as only mild in intensity it does limit the dose of inhaled agent given.

Accordingly, there is still a need for improved $M_3$ receptor antagonists that would have an appropriate pharmacological profile, for example in term of potency, pharmacokinetics or duration of action. In this context, the present invention relates to novel $M_3$ receptor antagonists. There is a need for $M_3$ receptor antagonists that would have a pharmacological profile suitable for an administration by the inhalation route.

The invention relates to the hydrochloride salt of 5-[3-(3-Hydroxyphenoxy)azetidin-1-yl]-5-methyl-2,2-diphenylhexanamide, and its derived forms.

Preferably the invention relates to a crystalline form of the hydrochloride salt of 5-[3-(3-Hydroxyphenoxy)azetidin-1-yl]-5-methyl-2,2-diphenylhexanamide.

Preferably the invention relates to a non solvated crystalline form of the hydrochloride salt of 5-[3-(3-Hydroxyphenoxy)azetidin-1-yl]-5-methyl-2,2-diphenylhexanamide.

Preferably, the hydrochloride salt of the invention has an X-ray diffraction pattern characterized by the following principal x-ray diffraction pattern peaks expressed in terms of 2-theta angle when measured using Cu $K\alpha_1$ radiation (Wavelength=1.5406 Å)

| Angle 2-Theta ° |
|---|
| 9.1 |
| 11.2 |
| 13.7 |
| 18.3 |
| 19.7 |

Preferably, the hydrochloride salt of the invention has an X-ray diffraction pattern characterized by the following principal x-ray diffraction pattern peaks expressed in terms of 2-theta angle when measured using Cu $K\alpha_1$ radiation (Wavelength=1.5406 Å):

| Angle 2-Theta ° |
|---|
| 7.5 |
| 9.1 |
| 11.2 |
| 13.7 |
| 14.8 |
| 18.3 |
| 19.7 |

Preferably, the hydrochloride salt of the invention has an X-ray diffraction pattern characterized by the following principal x-ray diffraction pattern peaks expressed in terms of 2-theta angle when measured using Cu $K\alpha_1$ radiation (Wavelength=1.5406 Å):

| Angle 2-Theta ° |
|---|
| 7.5 |
| 9.1 |
| 11.2 |
| 13.7 |
| 14.8 |
| 18.3 |
| 19.7 |
| 23.4 |
| 28.3 |

It has now been found that the the hydrochloride salt of the invention is an antagonist of the $M_3$ receptor, that is particularly useful for the treatment of $M_3$-mediated diseases and/or conditions, and shows good potency, in particular when administered via the inhalation route. The hydrochloride salt of the invention is particularly suitable for an administration by the inhalation route. In particular, the hydrochloride salt of the invention can be formulated for an administration using a dry powder inhaler.

The hydrochloride salt of the invention exhibits properties including those of solid state stability and compatibility with certain drug product excipient that render it superior to its corresponding free base.

The hydrochloride salt of the invention may be prepared from 5-[3-(3-Hydroxyphenoxy)azetidin-1-yl]-5-methyl-2,2-diphenylhexanamide according to conventional processes for the preparation of salts such as those disclosed in "Handbook of Pharmaceutical Salts, Properties, Selection and Use. Published by Wiley-VCH, 2002. Edited by P. Heinrich Stahl, Camille G Wermuth. ISBN 3-906390-26-8".

The hydrochloride salt of 5-[3-(3-Hydroxyphenoxy)azetidin-1-yl]-5-methyl-2,2-diphenylhexanamide may exist in both unsolvated and solvated forms. The term 'solvate' is used herein to describe a molecular complex comprising the hydrochloride salt of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Polymorphs and crystal morphologies/habits of the hydrochloride salt of the invention are also included within the scope of the invention.

The term "hydrochloride salt of the invention" includes the hydrochloride salt of 5-[3-(3-hydroxyphenoxy)azetidin-1-yl]-5-methyl-2,2-diphenylhexanamide and its derived forms.

The hydrochloride salt of the invention is a valuable pharmaceutically active compound, which is suitable for the therapy and prophylaxis of numerous disorders in which muscarinic receptors are involved or in which antagonism of this receptor may induce benefit, in particular the allergic and non-allergic airways diseases (e.g. asthma, COPD . . . ) but also in the treatment of other diseases such as Inflammatory Bowel Disease, Irritable Bowel Disease, diverticular disease, motion sickness, gastric ulcers, radiological examination of the bowel, symptomatic treatment of BPH (benign prostatic hyperplasia), NSAID induced gastric ulceration, urinary incontinence (including urgency, frequency, urge incontinence, overactive bladder, nocturia and lower urinary tract symptoms), cycloplegia, mydriatics and parkinsons disease.

The hydrochloride salt of the invention can be administered according to the invention to animals, preferably to mammals, and in particular to humans, as pharmaceutical for therapy and/or prophylaxis. It can be administered per se, in mixtures with one another or in the form of pharmaceutical preparations which as active constituent contain an efficacious dose of the hydrochloride salt of the invention, in addition to customary pharmaceutically innocuous excipients and/or additives.

The hydrochloride salt of the invention may be freeze-dried, spray-dried, or evaporatively dried to provide a solid plug, powder, or film of crystalline or amorphous material. Microwave or radio frequency drying may be used for this purpose.

The hydrochloride salt of the invention may be administered alone or in combination with other drugs and will generally be administered as a formulation in association with one or more pharmaceutically acceptable excipients. The term "excipient" is used herein to describe any ingredient other than the hydrochloride salt of the invention. The choice of excipient will to a large extent depend on the particular mode of administration.

The hydrochloride salt of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Formulations for parenteral administration may be formulated to be immediate and/or modified release. Modified release formulations include delayed-, sustained-, pulsed-, controlled-, targeted and programmed release. Thus the hydrochloride salt of the invention may be formulated as a solid, semi-solid, or thixotropic liquid for administration as an implanted depot providing modified release of the active compound. Examples of such formulations include drug-coated stents and PGLApoly(dl-lactic-coglycolic)acid (PGLA) microspheres.

The hydrochloride salt of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The hydrochloride salt of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the hydrochloride salt of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the hydrochloride salt of the invention per actuation and the actuation volume may vary from 1 µl to 100 µl. A typical formulation may comprise the hydrochloride salt of the invention, propylene glycol, sterile, water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the hydrochloride salt of the invention. The overall daily dose will typically be in the range 0.001 mg to 40 mg which may be administered in a single dose or, more usually, as divided doses throughout the day. The hydrochloride salt of the invention is particularly suitable for an administration by inhalation. In particular, the hydrochloride salt of the invention is suitable for a formulation with lactose as a dry powder and can thus be administered using a dry powder inhaler.

The hydrochloride salt of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The hydrochloride salt of the invention may also be administered, directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as liposomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The hydrochloride salt of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains the hydrochloride salt of the invention, may conveniently be combined in the form of a kit suitable for coadministration of the compositions.

Thus the kit of the invention comprises two or more separate pharmaceutical compositions, at least one of which contains the hydrochloride salt of the invention in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the hydrochloride salt of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the hydrochloride salt of the invention or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough.

As used herein, the terms "co-administration", "co-administered" and "in combination with", referring to the hydrochloride salt of the invention and one or more other therapeutic agents, is intended to mean, and does refer to and include the following:

simultaneous administration of such combination of hydrochloride salt of the invention and therapeutic agent(s) to a patient in need of treatment, when such components are formulated together into a single dosage form which releases said components at substantially the same time to said patient, substantially simultaneous administration of such combination of hydrochloride salt of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination of hydrochloride salt of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of hydrochloride salt of the invention and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (I), or pharmaceutically acceptable salts, derived forms or compositions thereof, include, but are by no means limited to:
  (a) 5-Lipoxygenase (5-LO) inhibitors or 5-lipoxygenase activating protein (FLAP) antagonists,
  (b) Leukotriene antagonists (LTRAs) including antagonists of $LTB_4$, $LTC_4$, $LTD_4$, and $LTE_4$,
  (c) Histamine receptor antagonists including H1 and H3 antagonists,
  (d) $\alpha_1$- and $\alpha_2$-adrenoceptor agonist vasoconstrictor sympathomimetic agents for decongestant use,
  (e) short or long acting $\beta_2$ agonists,
  (f) PDE inhibitors, e.g. PDE3, PDE4 and PDE5 inhibitors,
  (g) Theophylline,
  (h) Sodium cromoglycate,
  (i) COX inhibitors both non-selective and selective COX-1 or COX-2 inhibitors (NSAIDs),
  (j) Oral and inhaled glucocorticosteroids,
  (k) Monoclonal antibodies active against endogenous inflammatory entities,
  (l) Anti-tumor necrosis factor (anti-TNF-$\alpha$) agents,
  (m) Adhesion molecule inhibitors including VLA-4 antagonists,
  (n) Kinin-$B_1$- and $B_2$-receptor antagonists,
  (o) Immunosuppressive agents,
  (p) Inhibitors of matrix metalloproteases (MMPs),
  (q) Tachykinin $NK_1$, $NK_2$ and $NK_3$ receptor antagonists,
  (r) Elastase inhibitors,
  (s) Adenosine A2a receptor agonists,
  (t) Inhibitors of urokinase,
  (u) Compounds that act on dopamine receptors, e.g. D2 agonists,
  (v) Modulators of the NF$\kappa$B pathway, e.g. IKK inhibitors,
  (w) modulators of cytokine signalling pathyways such as p38 MAP kinase or syk kinase,
  (x) Agents that can be classed as mucolytics or anti-tussive,
  (y) Antibiotics,
  (z) HDAC inhibitors,
  (aa) PI3 kinase inhibitors, and,
  (bb) CXCR2 antagonists.

According to the present invention, combination of the compounds of formula (I) with:
  H3 antagonists,
  $\beta_2$ agonists,
  PDE4 inhibitors,
  steroids, especially glucocorticosteroids,
  Adenosine A2a receptor agonists,
  Modulators of cytokine signalling pathyways such as p38 MAP kinase or syk kinase, or,
  Leukotriene antagonists (LTRAs) including antagonists of $LTB_4$, $LTC_4$, $LTD_4$, and $LTE_4$, are preferred.

According to the present invention, combination of the compounds of formula (I) with:
  glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
  $\beta_2$ agonists including in particular salbutamol, terbutaline, bambuterol, fenoterol, salmeterol, formoterol, tulobuterol and their salts.

are further preferred.

It is to be appreciated that all references herein to treatment include curative, palliative and prophylactic treatment. The description, which follows, concerns the therapeutic applications to which the hydrochloride salt of the invention may be put.

The hydrochloride salt of the invention has the ability to interact with the M3 receptor and thereby have a wide range of therapeutic applications, as described further below, because of the essential role which the hydrochloride salt plays in the physiology of all mammals.

Therefore, a further aspect of the present invention relates to the hydrochloride salt of the invention or compositions thereof, for use in the treatment of diseases, disorders, and conditions in which the M3 receptor is involved. More specifically, the present invention also concerns the hydrochloride salt of the invention, for use in the treatment of diseases, disorders, and conditions selected from the group consisting of:

chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the hydrochloride salt of the invention, for the manufacture of a drug having a M3 antagonist activity. In particular, the present inventions concerns the use of the hydrochloride salt of the invention, or derived forms thereof, for the manufacture of a drug for the treatment of M3 receptor-mediated diseases and/or conditions, in particular the diseases and/or conditions listed above.

As a consequence, the present invention provides a particularly interesting method to treat a mammal, including a human being, with an effective amount of the hydrochloride salt of the invention, or a composition thereof. More precisely, the present invention provides a particularly interesting method for the treatment of a M3 receptor-mediated diseases and/or conditions in a mammal, including a human being, in particular the diseases and/or conditions listed above, comprising administering said mammal with an effective amount of the hydrochloride salt of the invention.

EXAMPLE 1

5-[3-(3-Hydroxy-phenoxy)-azetidin-1-yl]-5-methyl-2,2-diphenyl-hexanoic acid amide hydrochloride To a solution of 5-[3-(3-Hydroxy-phenoxy)-azetidin-1-yl]-5-methyl-2,2-diphenyl-hexanoic acid amide (3.5 g, 7.8 mmol) in methanol (30 ml) was added a 1.25M HCl solution in methanol (6.3 ml, 7.8 mmol). The solution was stirred at rt for 3 h then placed in an ice bath for 6 h. As no precipitation was noticed, the solution was concentrated under reduced pressure to remove some solvent (17 ml) and the resulting solution stirred at rt for 16 h to afford a precipitate. The suspension was filtered, washed with methanol (10 ml) and dried in a vacuum oven at 40° C. to give 5-[3-(3-Hydroxy-phenoxy)-azetidin-1-yl]-5-methyl-2,2-diphenyl-hexanoic acid amide hydrochloride as a white solid, 2.55 g (67%).

Figure 3:
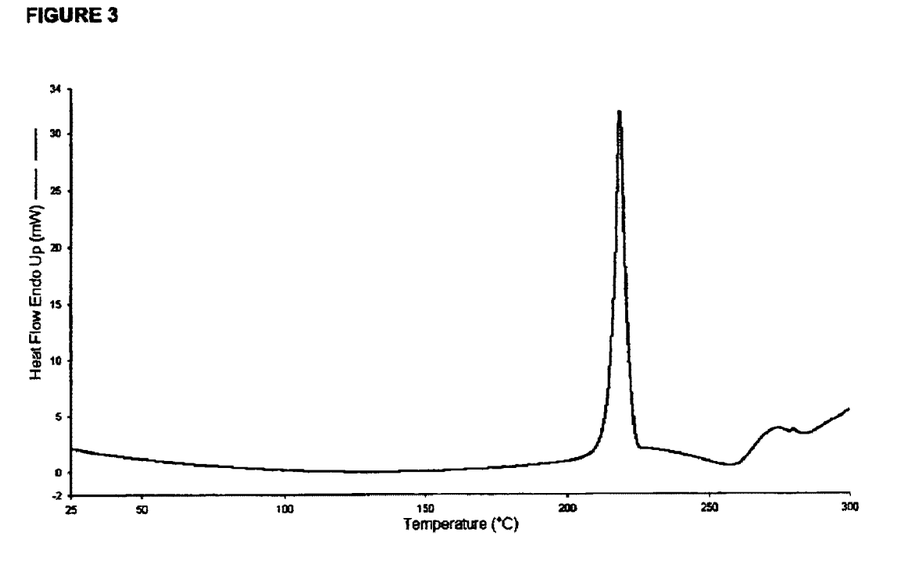
FIG. 3. DSC trace of example 1.

The melting point of example 1 was determined by Differential Scanning Calorimetry (DSC) using a Perkin Elmer Diamond Differential Scanning Calorimeter. The sample was heated at 20° C./minute, from ambient to 300° C., in a 50 μl vented aluminium pan. The DSC trace is shown in FIG. 3. The melting point was evidenced by a strong endotherm at 218.7° C. (onset at 215.3° C.).

Powder X-Ray Diffraction Method

Figure 1:
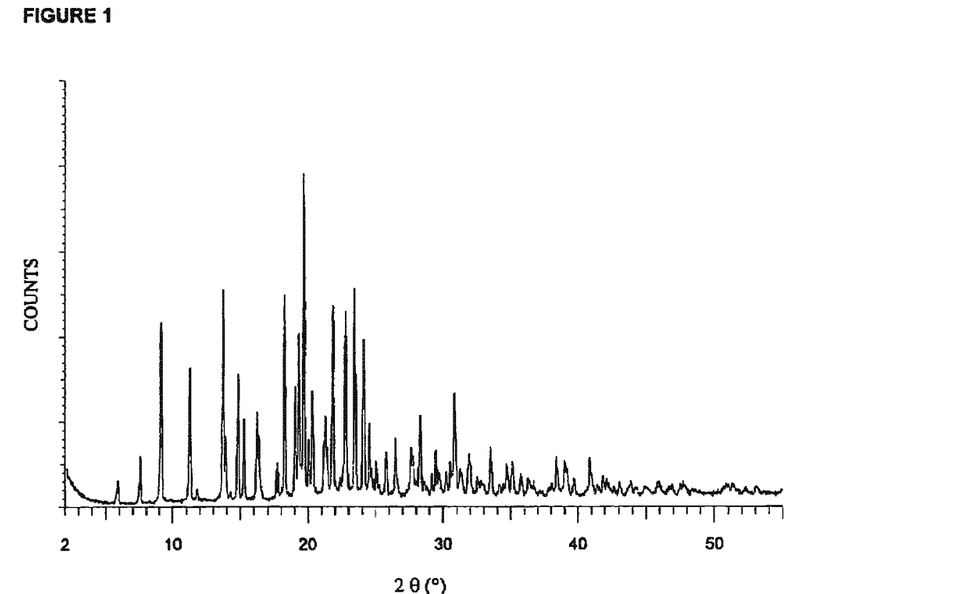
FIG. 1. XPRD pattern of example 1.

The powder X-ray diffraction pattern was measured using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background silicon wafer specimen mount. The specimen was rotated whilst being irradiated with Cu Kα1 X-rays (wavelength=1.5406 Angstroms) with the X-ray tube operated at 40 kV/35 mA. The analyses were performed with the goniometer running in continuous mode set for a 0.2 second count per 0.018° step over a two theta range of 2° to 55°. The measured pattern is shown in FIG. 1. Resultant powder X-ray diffraction pattern with intensities and peaks location (angle 2θ error is +/−0.1 degrees) are shown in the table 1:

TABLE 1

| Angle 2-Theta ° | Intensity % |
|---|---|
| 7.5 | 15.9 |
| 9.1 | 55.6 |
| 11.2 | 42.5 |
| 13.7 | 65.6 |
| 13.9 | 21.8 |
| 14.2 | 5.5 |
| 14.8 | 40.6 |
| 15.3 | 27.0 |
| 16.2 | 29.2 |

TABLE 1-continued

| Angle 2-Theta ° | Intensity % |
|---|---|
| 16.4 | 23.1 |
| 17.7 | 14.1 |
| 18.3 | 64.1 |
| 19.0 | 36.7 |
| 19.3 | 52.3 |
| 19.5 | 14.2 |
| 19.7 | 100.0 |
| 20.1 | 20.9 |
| 20.3 | 35.4 |
| 21.3 | 28.0 |
| 21.5 | 18.7 |
| 21.8 | 60.9 |
| 22.8 | 59.4 |
| 23.4 | 65.9 |
| 24.1 | 50.9 |
| 24.5 | 25.5 |
| 25.0 | 14.6 |
| 25.8 | 17.0 |
| 26.5 | 21.2 |
| 27.6 | 18.4 |
| 27.7 | 16.6 |
| 28.3 | 28.1 |
| 29.5 | 17.8 |
| 30.5 | 14.2 |
| 30.9 | 35.1 |
| 31.3 | 12.4 |
| 32.0 | 16.6 |
| 33.6 | 18.6 |
| 34.8 | 12.6 |
| 35.2 | 14.2 |
| 38.4 | 15.8 |
| 39.1 | 13.4 |
| 40.9 | 14.4 |

Crystal Structure Determination by Single Crystal X-Ray Diffraction

The crystal structure of Example 1 was determined by Single Crystal X-Ray diffraction at room temperature using a Bruker SMART APEX Single Crystal X-Ray diffractometer and Mo Kα radiation. Intensities were intergrated[1] from several series of exposures where each exposure covered 0.3° in ω, with an exposure time of 30 s and the total data set was more than a hemisphere. Data were corrected for absorption using the multiscans method.[2] The crystal structure was successfully solved by direct methods using SHELXS-97,[3] in Space Group $P2_12_12_1$ and refined by the method of least-squares using SHELXL-97.[4]

1. SMART v5.622 (control) and SAINT v6.02 (integration) software, Bruker AXS Inc., Madison, Wis. 1994.
2. SADABS, Program for scaling and correction of area detector data, G. M. Sheldrick, University of Göttingen, 1997 (based on the method of R. H. Blessing, *Acta Cryst.* 1995, A51, 33-38).
3. SHELXS-97, Program for crystal structure solution. G. M. Sheldrick, University of Göttingen, Germany, 1997, release 97-2.
4. SHELXL-97, Program for crystal structure refinement. G. M. Sheldrick, University of Göttingen, Germany, 1997, release 97-2.

Calculation of the Powder X-Ray Diffraction Pattern from the Example 1 Crystal Structure 2θ angles and relative intensities were calculated from the single crystal structure of Example 1 using the "Reflex Powder Diffraction" module of Accelrys MS Modelling™ [version 3.0].

Pertinent simulation parameters were:
Wavelength=1.5406 Å(Cu Kα)
Polarisation Factor=0.5
Pseudo-Voigt Profile (U=0.01, V=-0.001, W=0.002)

Figure 2:
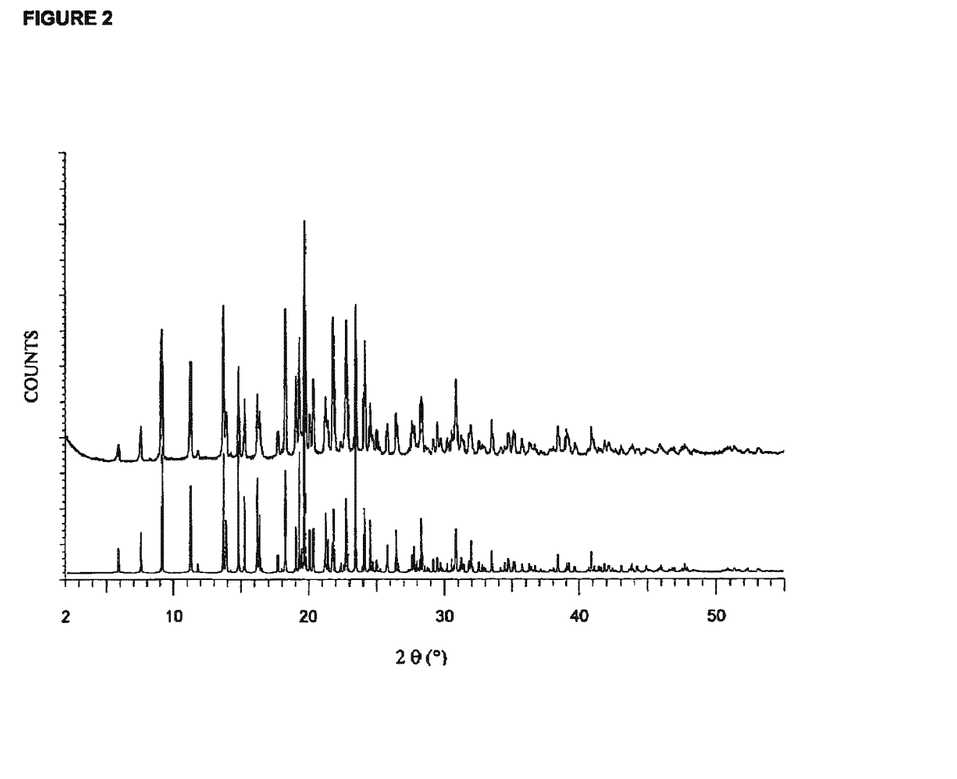
FIG. 2. XPRD pattern of example 1 vs calculated pattern from single crystal structure.

The calculated pattern represents that of a pure phase of Example 1 since it is derived from a single crystal structure. A comparison of the measured and calculated patterns is shown in FIG. 2 and demonstrates that the bulk is represented by the single crystal structure. Slight discrepancies between peak intensities can be attributed to preferred orientation effects is the measured pattern. FIG. 2 shows PXRD patterns of Example 1 (TOP: measured pattern BOTTOM: Calculated pattern from the single crystal structure).

Preparation 1: 5-[3-(3-Hydroxyphenoxy)azetidin-1-yl]-5-methyl-2,2-diphenylhexanamide A suspension of 5-[3-(3-Hydroxyphenoxy)azetidin-1-yl]-5-methyl-2,2-diphenyl-hexanenitrile (0.16 g, 0.38 mmol, 1 equiv), t-amyl alcohol (1.8 ml, 12 ml/g) and KOH (0.41 g, 7.26 mmol, 20 equiv) was heated to 80° C. for 2 d whereupon HPLC showed completion of reaction. The reaction was cooled to ambient then partitioned between water and TBME, the aqueous layer was acidified to pH 8 with aq HCl, layers separated and the organic layer concentrated to afford 5-[3-(3-Hydroxyphenoxy)azetidin-1-yl]-5-methyl-2,2-diphenyl-hexanamide as a colourless oil, 0.11 g (68%).
¹HNMR (400 MHz, CDCl₃) δ: 1.10 (s, 6H), 1.22-1.34 (m, 2H), 2.42-2.55 (m, 2H, 3.28-3.40 (m, 2H), 3.65-3.88 (m, 2H), 4.70-4.80 (m, 1H), 5.55-5.70 (brs, 2H), 6.23-6.36 (m, 2H), 6.45-6.53 (m, 1H), 7.03-7.12 (m, 1H), 7.19-7.39 (m, 10H); LRMS ESI m/z 445 [M+H]⁺

Preparation 2: 5-[3-(3-Hydroxyphenoxy)azetidin-1-yl]-5-methyl-22-diphenyl-hexanenitrile

To methanesulfonic acid (200 ml, 5 ml/g) at ambient temp under an atmosphere of nitrogen was added 5-[3-(3-Methoxyphenoxy)azetidin-1-yl]-5-methyl-2,2-diphenyl-hexanenitrile (40 g, 90.13 mmol, 1 equiv) then DL-methionine (40.6 g, 272 mmol, 3 equiv) resulting in a solution. The solution was stirred for 3 d at ambient and 1 d at 30° C. before adding further DL methionine (5.42 g, 36 mmol, 0.4 equiv) and maintaining at 30° C. for a further 2 d whereupon HPLC indicated reaction completion (<5% SM).

The mixture was diluted with i-PrOAc (400 ml) then with care water (400 ml). The layers were mixed for 15 mins then separated. Organic layer was washed with 1M NaOH (400 ml) then water (2×200 ml) before drying over MgSO₄ and concentrating to a white solid under reduced pressure at 40° C. The solid was re-suspended in toluene (160 ml, 4 ml/g) at −5° C. for 1 hour then filtered, washed with cold toluene (80 ml, 2 ml/g) and dried in a vacuum oven at 50° C. for 2 days to give 5-[3-(3-Hydroxyphenoxy)azetidin-1-yl]-5-methyl-2,2-diphenyl-hexanenitrile as a white solid, 29.3 g (76%). Analysis by HPLC shows >98% area.

$^1$HNMR (300 MHz, CDCl$_3$) δ: 0.98 (s, 6H), 1.35-1.44 (m, 2H), 2.41-2.52 (m, 2H), 3.18-3.26 (m, 2H), 3.48-3.57 (m, 2H), 4.65-4.74 (m, 1H), 6.26-6.29 (m, 1H), 6.32-6.37 (m, 1H), 6.43-6.47 (m, 1H), 7.12 (t, J 8.2 Hz, 1H), 7.25-7.44 (m, 10H)

Preparation 3: 5-[3-(3-Methoxyphenoxy)azetidin-1-yl]-5-methyl-2,2-diphenyl-hexanenitrile To THF (700 ml) under a N$_2$ atmosphere cooled in an ice bath was added ZrCl$_4$ (80.4 g, 0.35 mol, 2.1 equiv) portion-wise maintaining a temp below 15° C. and resulting in a brown suspension. The mixture was then cooled further in an ice/MeOH bath before addition of MeMgCl (3M in THF, 493 ml, 1.48 mol, 9 equiv) over 1 h maintaining temp below 0° C. To the Zr/Grignard solution was slowly added a pre-formed solution of 5-[3-(3-Methoxyphenoxy)azetidin-1-yl]-5-oxo-2,2-diphenyl-pentanenitrile (70 g, 0.164 mol, 1 equiv) in THF (210 ml, 3 ml/g) controlling the exotherm to below 0° C. The resulting brown suspension was maintained at 0° C. for 6.5 h before Me-THF (700 ml) was added followed by careful quench with aq.NH$_4$Cl (pre-made with 400 ml sat.NH$_4$Cl+ 500 ml water). Upon separation the organic layer was washed with water (3×350 ml), dried over MgSO$_4$ and solvent exchanged into EtOH at 40° C. under reduced pressure resulting in a precipitate of final volume 210 ml (3 ml/g). The suspension was stirred at ambient for 18 h then cooled in an ice bath for 1 h, filtered, washed with EtOH (140 ml, 2 ml/g) and dried in a vacuum oven at 45° C. for 5 h to give 5-[3-(3-Methoxyphenoxy)azetidin-1-yl]-5-methyl-2,2-diphenyl-hexanenitrile as a white solid, 43.1 g (60%). Analysis by HPLC shows >99% area.

$^1$HNMR (400 MHz, CDCl$_3$) δ: 0.90-1.03 (m, 6H), 1.31-1.44 (m, 2H), 2.41-2.56 (m, 2H), 3.07-3.24 (m, 2H), 3.42-3.54 (m, 2H), 3.77 (s, 3H), 4.63-4.74 (m, 1H), 6.28-6.38 (m, 2H), 6.48-6.55 (m, 1H), 7.26-7.49 (m, 11H); LRMS APCI m/z 441 [M+H]$^+$

Preparation 4: 5-[3-(3-Methoxyphenoxy)azetidin-1-yl]-5-oxo-2,2-diphenyl-pentanenitrile To a suspension of 4-Cyano-4,4-diphenyl-butyric acid (300 g, 1.13 mol, 1 equiv) in EtCN (3.0 L, 3 ml/g) at rt was added DMAP (13.82 g, 0.11 mol, 0.1 equiv)), 3-(3-Methoxyphenoxy)azetidine hemi-oxalate (253.5 g, 1.13 mol, 1 equiv) then WSCDI (325.2 g, 1.68 mol, 1.5 equiv) resulting in slight effervescence, a 10° C. exotherm and dissolution to a solution. After 2 h the reaction was deemed complete by HPLC (no amine detected). 2M HCl (1.2 L, 4 ml/g) was added and the biphasic mixture stirred for 10 mins before separating, washing the organic layer with 2M NaOH (1.5 L, 5 ml/g) and water (2×1.5 L).

The solution was concentrated to dryness under reduced pressure at 40° C. and replaced with MeOH. This was repeated to remove all EtCN, and the resulting hot methanolic solution of volume 2.5 L (8.33 ml/g) was allowed to cool resulting in a thick suspension. The suspension was cooled in an ice bath for 2 h then filtered, washed with MeOH (600 ml, 2 ml/g) and the solid dried under vacuum for 18 h at 45° C. to give 5-[3-(3-Methoxyphenoxy)azetidin-1-yl]-5-oxo-2,2-diphenyl-pentanenitrile as a white solid, 347 g (72%). Analysis by HPLC shows >98% area.

$^1$HNMR (300 MHz, d$_6$-dmso) δ: 2.07-2.16 (m, 2H), 2.69-2.77 (m, 2H), 3.70-3.78 (m, 1H), 3.72 (s, 3H), 3.94-4.00 (m, 1H), 4.21-4.29 (m, 1H), 4.42-4.45 (m, 1H), 4.92-5.00 (m, 1H), 6.36-6.42 (m, 2H), 6.54-6.59 (m, 1H), 7.16-7.23 (m, 1H), 7.30-7.40 (m, 2H), 7.41-7.46 (m, 8H)

Preparation 5: 3-(3-Methoxyphenoxy)azetidine hemi-oxalate

To a suitable hydrogenation vessel was added 1-Benzhydryl-3-(3-methoxyphenoxy)azetidine (300 g, 0.87 mol, 1 equiv), Pd(OH)$_2$ (20% wt on Carbon) (60 g, 20% wt) and EtOH (6 L, 20 ml/g). The mixture was placed under 60 psi H$_2$ and stirred at rt until reaction completion after 48 h (<5% SM by HPLC).

The reaction mixture was filtered over Arbocel and washed with copious EtOH, then concentrated to a volume of 1.2 L (4 ml/g) under reduced pressure at 40° C. To the resulting solution to ambient was added oxalic acid (39.11 g, 0.43 mmol, 0.5 equiv) potion-wise resulting in a thick suspension and a 15° C. exotherm, the mixture was left to stir for 3 d at rt. The suspension was cooled in an ice bath for 2 h then filtered, washed with EtOH (600 ml, 2 ml/g) and the solid dried under vacuum at 50° C. for 18 h to give 3-(3-Methoxyphenoxy) azetidine hemi-oxalate as a white solid, 165 g (85%). Analysis by HPLC shows >96% area.

Preparation 6:
1-Benzhydryl-3-(3-methoxyphenoxy)azetidine

To a solution of methanesulfonic acid 1-benzhydryl-azetidin-3-yl ester (1169 g, 3.68 mol, 1 equiv) in EtCN (2.33 L, 2 ml/g) at it was added $K_2CO_3$ (610.6 g, 4.42 mol, 1.2 equiv). To the resulting slurry was added a pre-formed solution of 3-methoxyphenol (548.3 g, 4.42 mol, 1.2 equiv) in EtCN (3.50 L, 3 ml/g) and the mixture heated to 80° C. under a $N_2$ atmosphere for 18 h, whereupon reaction completion was observed (<5% methanesulfonic acid 1-benzhydryl-azetidin-3-ylester by HPLC).

Upon cooling to ambient 1M NaOH (5.85 L, 5 ml/g) was added and the resulting solution stirred for ~15 mins before allowing to separate. The layers were partitioned and the organic layer washed with 1M NaOH (3.51 L, 3 ml/g) and aq.brine (116 g NaCl in 5.58 L water, 5 ml/g). The organic layer was placed under atmospheric distillation conditions and solvent exchanged into MeOH by concentration to low volume (2 ml/g) then sequential additions of MeOH, affording a 4 ml/g suspension with no EtCN detected by $^1$H NMR.

The suspension was cooled to 0° C. for 3 h then filtered, washed with MeOH (2.5 L) and the solid dried under vacuum at 50° C. for 18 h to give PF1261660 as a white solid, 944 g (74%). Analysis by HPLC shows >99% area.

ABBREVIATIONS

| | |
|---|---|
| rt = | room temperature |
| Me = | methyl |
| Ph = | phenyl |
| SM = | starting material |
| h = | hour |
| mins = | minutes |
| d = | day |

In Vitro Activity of the Hydrochloride Salt of the Invention
Potency Assay $M_3$ potency is determined in CHO-K1 cells transfected with the NFAT-Betalactamase gene. CHO (Chinese Hamster Ovary) cells recombinantly expressing the human muscarinic $M_3$ receptor are transfected with the NFAT_β-Lac_Zeo plasmid. Cells are grown in DMEM with Glutamax-1, supplemented with 25 mM HEPES (Life Technologies 32430-027), containing 10% FCS (Foetal Calf Serum; Sigma F-7524), 1 nM Sodium pyruvate (Sigma S-8636), NEAA (non-Essential Amino Acids; Invitrogen 11140-035) and 200 µg/ml Zemin (Invitrogen R250-01).

hM$_3$ β-Lac Assay Protocol

Cells are harvested for assay when they reach 80-90% confluency using enzyme free cell Dissociation Solution (Life technologies 13151-014) incubated with the cells for 5 min at 37° C. in an atmosphere containing 5% $CO_2$. Detached cells are collected in warmed growth media and centrifuged at 2000 rpm for 10 min, washed in PBS (Phosphate Buffered Saline; Life Technologies 14190-094) and centrifuged again as just described. The cells are re-suspended at $2 \times 10^5$ cells/ml in growth medium (composition as described above). 20 µl of this cell suspension is added to each well of a 384 well black clear bottomed plate (Greiner Bio One 781091-PFI). The assay buffer used is PBS supplemented with 0.05% Pluronic F-127 (Sigma 9003-11-6) and 2.5% DMSO. Muscarinic $M_3$ receptor signalling is stimulated using 80 nM carbamyl choline (Aldrich N240-9) incubated with the cells for 4 h at 37° C./5% $CO_2$ and monitored at the end of the incubation period using a Tecan SpectraFluor+plate reader (λ-excitation 405 nm, emission 450 nm and 503 nm). The compound to be tested is added to the assay at the beginning of the 4 h incubation period and compound activity measured as the concentration dependent inhibition of the carbamyl choline induced signal. Inhibition curves are plotted and $IC_{50}$ values generated using a 4-parameter sigmoid fit and converted to Ki values using the Cheng-Prusoff correction and the $K_D$ value for carbamyl choline in the assay.

Guinea Pig Trachea Assay

Male, Dunkin-Hartley guinea-pigs weighing 350-450 g are culled in a rising concentration of $CO_2$, followed by exsanguinations of the vena cava. Tracheas are dissected from the larynx to the entry point into the chest cavity and then placed in fresh, oxygenated, modified Krebs buffer solution (Krebs containing 10 µM propranolol, 10 µM guanethidine and 3 µM indomethacin) at room temperature. The tracheas are opened by cutting through the cartilage opposite the trachealis muscle. Strips approximately 3-5 cartilage rings wide are cut. A cotton thread is attached to the cartilage at one end of the strip for attachment to the force transducer and a cotton loop made at the other end to anchor the tissue in the organ bath. The strips are mounted in 5 ml organ baths filled with warm (37° C.) aerated modified Krebs. The pump flow rate is set to 1.0 ml/min and the tissues washed continuously. Tissues are placed under an initial tension of 1000 mg. Tissues are re-tensioned after 15 and 30 minutes, then allowed to equilibrate for a further 30-45 minutes.

Tissues are subjected to electrical field stimulation (EFS) of the following parameters: 10 s trains every 2 minutes, 0.1 ms pulse width, 10 Hz and 10-30V. The voltage is raised 5V every 10 min within the stated range until a maximum contractile response for each tissue is observed. This just maximum voltage for each tissue is then used throughout the remainder of the experiment. Following equilibration to EFS for 20 min, the pump is stopped, and after 15 min control readings are taken over a 8-10 min period (4-5 responses). Compound is then added to each tissue as a bolus dose at 30×Ki (determined at the human $M_3$ receptor expressed in CHO cells in a filtration binding assay), and left to incubate for 2 h. Compound is then washed from tissues using a rapid wash with modified Krebs for 1 min and flow is restored to 1 ml/min for the remainder of the experiment. At the end of the experiment tissues are challenged with histamine (1 µM) to determine viability. Readings taken during the experiment are automatically collected using Notocord® software. The raw data are converted into percent response taking into account measurements of inhibition of the EFS response. After starting washout, the times taken for the tissue to recover by 25% from the inhibition induced are recorded and used as a measure of compound duration of action. Tissue viability limits the duration of the experiment to 16 h post-compound washout. Compounds are typically tested at n=2 to 5 to estimate duration of action.

Alternatively the Following Guinea Pig Trachea Assay Can Also Be Used:

Trachea are removed from male Dunkin-Hartley guinea-pigs (wt 350-450 g) and following removal of adherent connective tissue, an incision is made through the cartilage opposite the trachealis muscle and tracheal strips 3-5 cartilage rings wide prepared. The tracheal strips are suspended between an isometric strain gauge and a fixed tissue hook with the muscle in the horizontal plane in 5 ml tissue baths under an initial tension of 1 g and bathed in warmed (37° C.) aerated (95% $O_2$/5% $CO_2$) Krebs solution containing 3 μM indomethacin and 10 μM guanethidine.

The tissues are positioned between parallel platinum wire electrodes (~1 cm gap). A constant 1 ml/min flow of fresh Krebs solution (of the above composition) is maintained through the tissue baths using peristaltic pumps. The tissues are allowed to equilibrate for an hour with re-tensioning to 1 g at 15 min and 30 min from the start of the equilibration period. At the end of the equilibration, tissues are electrically field stimulated (EFS) using the following parameters: 10V, 10 Hz 0.1 ms pulse width with 10 sec trains every 2 min. In each tissue a voltage response curve is constructed over the range 10 v-30V (keeping all other stimulation parameters constant) to determine a just maximal stimulation. Using these stimulation parameters EFS responses are 100% nerve mediated and 100% cholinergic as confirmed by blockade by 1 μM tetrodotoxin or 1 μM atropine. Tissues are then repeatedly stimulated at 2 min intervals until the responses were reproducible. The peristaltic pump is stopped 20 min prior to the addition of the study compound and the average twitch contraction over the last 10 min recorded as the control response. The study compound is added to the tissue baths, with each tissue receiving a single concentration of compound and allowed to equilibrate for 2 h. At 2 h post addition the inhibition of the EFS response is recorded and $IC_{50}$ curves generated using a range of compound concentrations over tracheal strips from the same animal. The tissues are then rapidly washed and the 1 ml/min perfusion with Krebs solution re-established. Tissues are stimulated for a further 16 h and recovery of the EFS response recorded. At the end of the 16 h, 10 μM histamine is added to the baths to confirm tissue viability. The just max concentration (tested concentration giving a response >70% inhibition but less than 100%) of antagonist is identified from the $IC_{50}$ curve and the time to 25% recovery of the induced inhibition ($T_{25}$) calculated in tissues receiving this concentration. Compounds are typically tested at n=2 to 5 to estimate duration of action.

The invention claimed is:

1. Hydrochloride salt of 5-[3-(3-hydroxyphenoxy)azetidin-1-yl]-5-methyl-2,2-diphenyl hexanamide having a melting point endotherm at about 218.7° C.

2. A non solvated crystalline hydrochloride salt of 5-[3-(3-hydroxyphenoxy)azetidin-1-yl]-5-methyl-2,2-diphenyl hexanamide having an X-ray diffraction pattern comprising the following principal X-ray diffraction pattern peaks expressed in terms of 2-theta angle when measured using Cu K$\alpha_1$ radiation (Wavelength=1.5406 Å)

| Angle 2-Theta (+/−0.1 degrees) |
| --- |
| 9.1 |
| 11.2 |
| 13.7 |
| 18.3 |
| 19.7. |

3. A pharmaceutical composition comprising at least an effective amount of a compound according to claim 1.

4. A pharmaceutical composition comprising at least an effective amount of a compound according to claim 2.

5. A method of treating a disease, disorder or condition in a mammal, said method comprising administering to said mammal in need thereof a therapeutically effective amount a M3 antagonist of claim 1 wherein said disease, disorder or condition is selected from chronic bronchoconstriction acute bronchoconstriction, small airways obstruction, emphysema, obstructive or inflammatory airways diseases, bronchitis, asthma, acute lung injury, or bronchiectasis.

6. A method according to claim 5 where the disease, disorder or condition is asthma or chronic obstructive pulmonary disease (COPD).

7. A method of treating a disease, disorder or condition in a mammal, said method comprising administering to said mammal in need thereof a therapeutically effective amount a M3 antagonist of claim 2 wherein said disease, disorder or condition is selected from chronic bronchoconstriction acute bronchoconstriction, small airways obstruction, emphysema, obstructive or inflammatory airways diseases, bronchitis, asthma, acute lung injury, or bronchiectasis.

8. A method according to claim 7 where the disease, disorder or condition is asthma or chronic obstructive pulmonary disease (COPD).

* * * * *